United States Patent
Liu et al.

(10) Patent No.: US 9,333,108 B2
(45) Date of Patent: May 10, 2016

(54) VERTEBRA HEALTH BODY SUIT

(76) Inventors: Fangguo Liu, Xiamen (CN); Bin Liu, Xiamen (CN)

( * ) Notice: Subject to any disclaimer, the term of this patent is extended or adjusted under 35 U.S.C. 154(b) by 388 days.

(21) Appl. No.: 13/806,587

(22) PCT Filed: May 19, 2011

(86) PCT No.: PCT/CN2011/074287
§ 371 (c)(1),
(2), (4) Date: Dec. 21, 2012

(87) PCT Pub. No.: WO2011/160515
PCT Pub. Date: Dec. 29, 2011

(65) Prior Publication Data
US 2013/0110021 A1    May 2, 2013

(30) Foreign Application Priority Data
Jun. 24, 2010    (CN) .......................... 2010 1 0208778

(51) Int. Cl.
*A61F 5/02* (2006.01)
*A61F 5/048* (2006.01)

(52) U.S. Cl.
CPC . *A61F 5/02* (2013.01); *A61F 5/026* (2013.01); *A61F 5/028* (2013.01); *A61F 5/048* (2013.01)

(58) Field of Classification Search
CPC .............. A61F 5/00; A61F 5/01; A61F 5/02; A61F 5/022; A61F 5/024; A61F 5/026; A61F 5/028; A61F 5/04; A61F 5/042; A61F 5/048; A61F 5/03; A61F 5/24; A61F 5/26; A61F 5/37; A61F 2005/0197
See application file for complete search history.

(56) References Cited

U.S. PATENT DOCUMENTS

| 903,403 | A | * | 11/1908 | Quick et al. ......................... 2/44 |
| 1,544,162 | A | * | 6/1925 | La Vigne ............................. 2/44 |
| 1,650,650 | A | * | 11/1927 | Pieper .............................. 602/19 |
| 1,722,205 | A | * | 7/1929 | Freund ................................ 2/44 |
| 5,405,313 | A | | 4/1995 | Albin |
| 5,462,518 | A | * | 10/1995 | Hatley et al. .................... 602/36 |
| 5,499,965 | A | | 3/1996 | Sanchez |
| 5,816,251 | A | | 10/1998 | Glisan |
| 5,916,188 | A | * | 6/1999 | Ousdal ............................ 602/32 |
| 6,280,405 | B1 | * | 8/2001 | Broselid ......................... 602/36 |
| 6,766,532 | B1 | | 7/2004 | Cabana |

(Continued)

FOREIGN PATENT DOCUMENTS

| CN | 2730341 Y | 10/2005 |
| CN | 200945203 Y | 9/2007 |

(Continued)

*Primary Examiner* — Nicholas Woodall
*Assistant Examiner* — Raymond E Harris
(74) *Attorney, Agent, or Firm* — Rabin & Berdo, P.C.

(57) ABSTRACT

A vertebra health body suit has a fixation part, a memory alloy support part, a spring part and a wearing part. The fixation part is removably surrounded to the waist of the user and supported on the pelvis of the user; the lower end of the memory alloy support part is fixed and supported on the fixation part; the spring part includes at least a first coil spring, the first coil spring is sleeved in the support part; and the wearing part is removably worn on the chest and the shoulder of the user, the wearing part is assembled in the upper end of the support part. With the longitudinal support by the memory alloy support part and the spring part, the gravity above the chest and the waist is supported by the pelvis to relieve the force of the waist.

6 Claims, 4 Drawing Sheets

(56) References Cited

U.S. PATENT DOCUMENTS

2002/0193165 A1* 12/2002 Yoshimura .................. 464/68
2003/0220594 A1* 11/2003 Halvorson et al. ........... 602/19
2006/0247637 A1* 11/2006 Colleran et al. ............. 606/61
2008/0195010 A1*  8/2008 Lai et al. ...................... 602/5
2011/0083250 A1*  4/2011 Smith et al. ................ 2/161.6

FOREIGN PATENT DOCUMENTS

| CN | 200945204 Y | 9/2007 |
| CN | 201230577 Y | 5/2009 |
| CN | 102008363 A | 4/2011 |
| EP | 2070495 A1 | 6/2009 |

* cited by examiner

VERTEBRA HEALTH BODY SUIT

CROSS-REFERENCE TO RELATED APPLICATIONS

This application is the national phase of PCT/CN2011/074287, filed May 19, 2011, and claims priority from CN 201010208778.3, filed Jun. 24, 2010, both of which are herein incorporated by reference.

BACKGROUND OF THE INVENTION

1. Field of the Invention

The present invention relates to a health device, especially to a vertebra health body suit.

2. Description of the Related Art

As the human body is suffered with the earth attraction, the self pressure and the negative gravity from the life and work, senile degenerative symptoms and pathology cause as the centrum and the tissue surrounded wear out. For example, the hypertension, lumbocrural pain and pain in lower limbs caused by rennin-angiogensin.

The ageing phenomenon is unavoidable. So there are several proposal in the market and the Chinese patent database, such as a lumbar tractor or a waist support, these existing technology has disadvantages as below: firstly, they are inconvenient to wear, and they limit the body movement, which limits the application and popularity of the devices; secondly, they are not cool in summer and warm in winter, they can be used in long term. They are difficult to be accepted.

SUMMARY OF THE INVENTION

The present invention is provided with a vertebra health body suit, which overcomes the problem of the existing health device, such as a lumbar tractor or a waist support, that the wearing is inconvenient.

The technical proposal of the present invention to overcome the technical problem is as below:

A vertebra health body suit includes:

A fixation part, which is removably surrounded to the waist of the user and supported on the pelvis of the user;

A memory alloy support part, the lower end of which is fixed and supported on the fixation part;

A spring part, which includes at least a first coil spring, the first coil spring is sleeved in the support part; and A wearing part, which is removably worn on the chest and the shoulder of the user, the wearing part is assembled in the upper end of the support part.

In another preferred embodiment, an inverted Y-shaped part is fixed in the lower of the support part, a Y-shaped part is fixed in the upper of the support part, the two lower ends of the inverted Y-shaped part is fixed to the fixation part, the two upper ends of the Y-shaped part is assembled to the wearing part.

In another preferred embodiment, the spring part further includes a second coil spring, the second coil spring forms a sleeve around the first coil spring.

In another preferred embodiment, the overhead projection of the first coil spring is ellipse shape, the overhead projection of the second coil spring is ellipse shape.

In another preferred embodiment, two adjacent spring rings of the first coil spring are connected closely; two adjacent spring rings of the second coil spring are connected closely.

In another preferred embodiment, the fixation part further includes a waist belt, a length adjustable buckle is disposed in the waist belt; the lower end of the support par is fixed and supported in the waist belt.

In another preferred embodiment, the wearing part includes a chest guard and two straps, the chest guard is disposed with a length adjustable buckle, the chest guard is fixed and supported in the upper end of the support part, the two ends of the strap are separately sewn in the chest guard.

Compared to the existing technology, the technical proposal of the present invention has advantages as below:

1. With the longitudinal support by the memory alloy support part and the spring part, the gravity above the chest and the waist is supported by the pelvis to relieve the force of the waist, and it has advantages as below: firstly, as the memory alloy support part and the spring part can be easily bended to coordinate with the body motion, it is convenient to wear, and it will not interfere with the body motion, even that it will assist the motoricity of the lumbar and thoracic vertebra; secondly, with long term usage, the present invention can protect the centrum and the tissue surrounded effectively, relieve the extrusion pressure between the centrums of the lumbar and the thoracic vertebra, stave off the production of the rennin angiotensin, stave off hypertension or other chronic degenerative diseases or other chronic strain caused by angiotension; it's mainly used for preventive treatment of disease and anti-aging and to prolong the life; thirdly, with the spring part, it protect the brain by shock absorption and shock proof; fourthly, the support part is made of memory alloy, that even bended in 360 degrees, it will not be broken down; it has well flexibility.

2. The spring part is disposed with two coil springs of sleeved connected, which had advantages as below: firstly it ensures the longitudinal support strength and the service life of the spring part; secondly it has good permeability and cool in summer and warm in winter; thirdly the support strength is better with two springs, it will not be broken with long term bending.

3. The overhead projection of the first coil spring and the second coil spring is ellipse shape to suit for the inner surface of the back of the user with comfortably.

4. The adjacent spring rings of the first and second coil spring are connected closely to strengthen the support strength;

5. An inverted Y-shaped part is fixed in the lower of the support part, a Y-shaped part is fixed in the upper of the support part, the support part is with high stability and solid construction.

6. The wearing part includes a chest guard and two straps, thereinto the chest guard is disposed with adjustable buckle according to the figure of the user; two straps are separately supported the shoulders of the user and fixed and supported in the upper end of the support part, with the straps and the chest guard, the gravity above the chest and waist of the user are supported over the support part, it is simple-structure, convenient, beautiful and cool in summer and warm in winter. It can be used in day and night.

BRIEF DESCRIPTION OF THE DRAWINGS

The present invention will be further described with the drawings and embodiments

REFERENCE SIGNS

Figure 1:
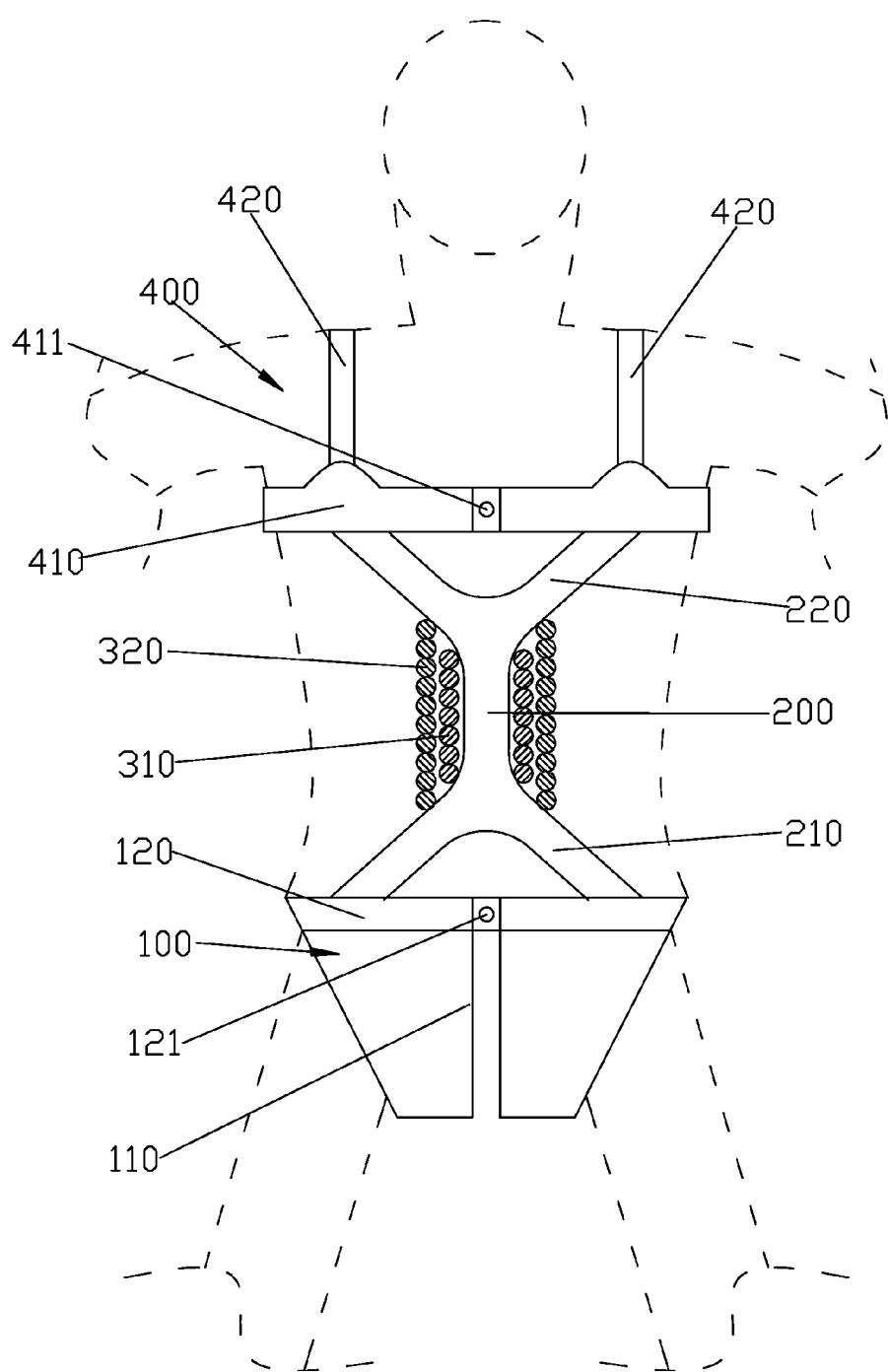
FIG. 1 illustrates the structure of the embodiment of the present invention.
Figure 2:
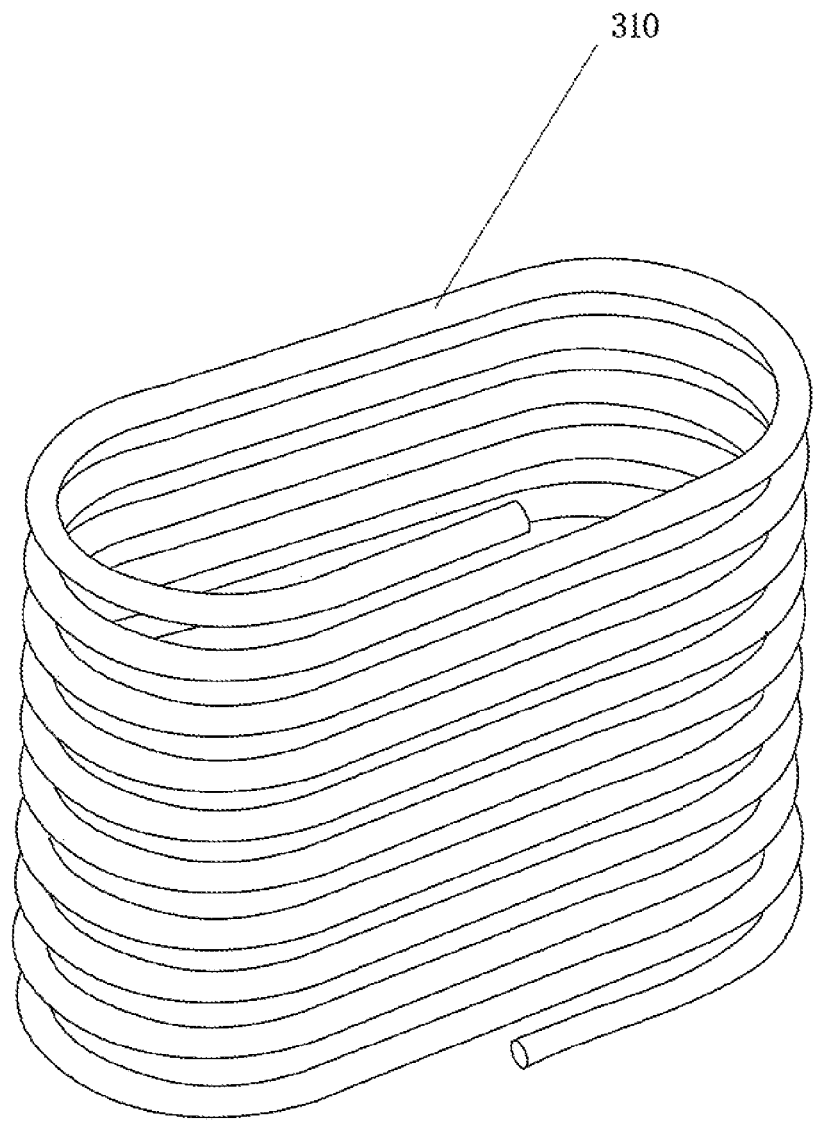
FIG. 2 illustrates the elliptical shape of the first coil spring.
Figure 3:
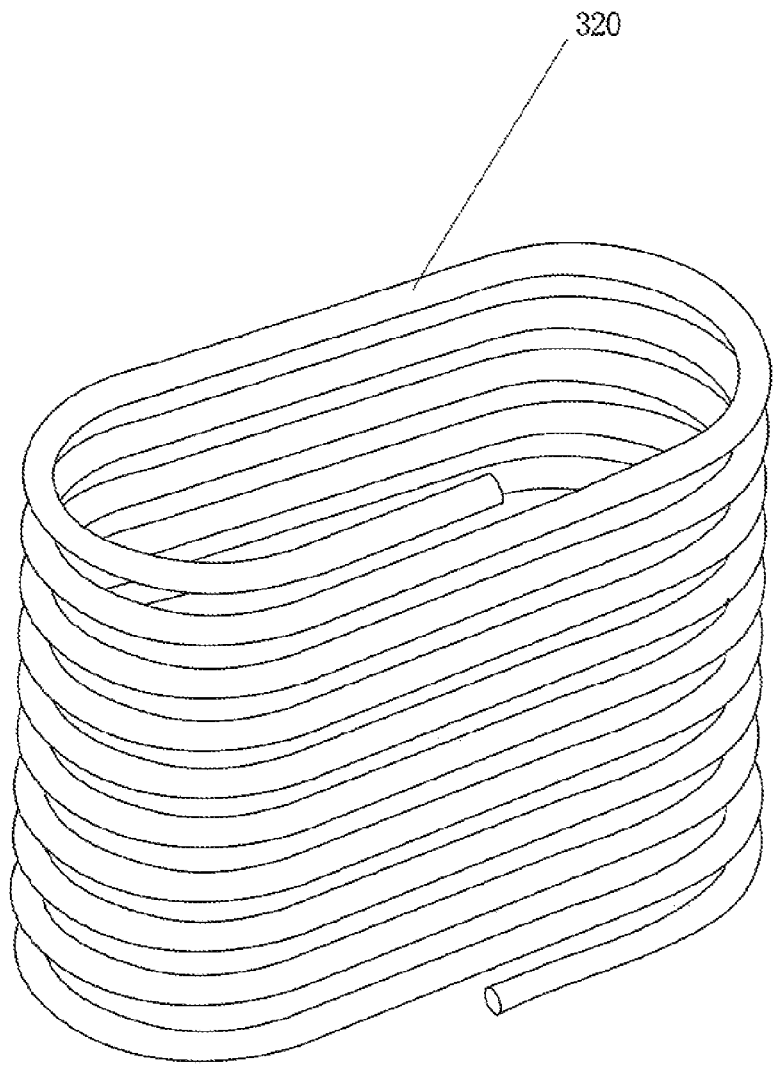
FIG. 3 illustrates the elliptical shape of the second coil spring.
Figure 4:
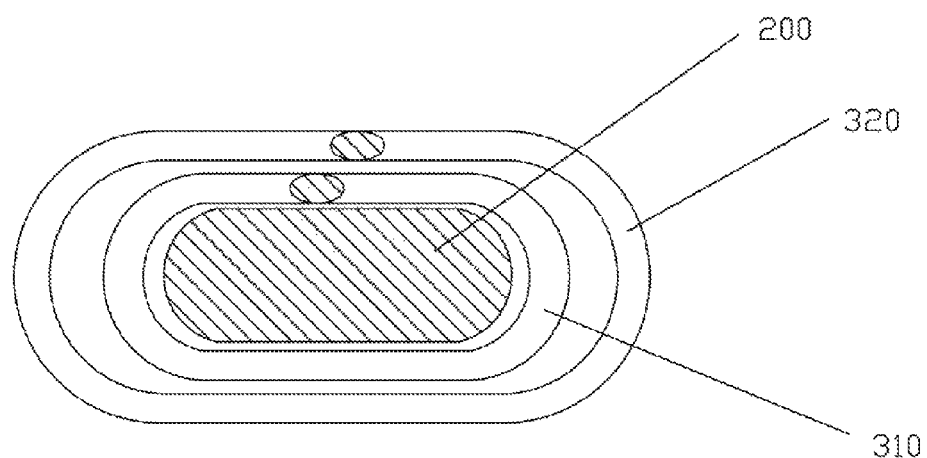
FIG. 4 illustrates a cross-section of the present invention.

The fixation part 100, the supporting part 200, the wearing part 400, the pelvis fixation belt 110, the waist belt 120, the first adjustable buckle 121, the inverted Y-shaped part 210, the Y-shaped part 220, the first coil spring 310, the second coil spring 320, the chest guard 410, the strap 420, the second adjustable buckle 411

DETAILED DESCRIPTION OF THE EMBODIMENTS

FIG. 1 illustrates the structure of the vertebra health body suit, which includes a fixation part 100, a support part 200, a spring part and a wearing part 400. In this embodiment, the support part 200 is made of memory alloy formed in one step; the memory alloy is titanium alloy.

The fixation part 100 includes a pelvis fixation belt 110 and a waist belt 120 fixed to the pelvis fixation belt 110. The waist belt 120 is disposed with a first adjustable buckle 121 to adjust the length of the waist belt 120 for user adaptation. When the pelvis fixation belt 110 is worn on the user, the waist belt 120 is surrounded at the waist of the user and supported over the pelvis. Two independent first assembly belts of faced up are disposed in the back part inside the waist belt 120.

The pelvis fixation belt 110 can be a shorts, the shorts is better an open-seat shorts so the user do not need to take off the body suit to go to the washroom.

An inverted Y-shaped part 210 is fixed in the lower end of the memory alloy support part 200; a Y-shaped part 220 is fixed in the upper end of the support part 200. Two lower ends of the inverted Y-shaped part 210 are separately inserted into the two first assembly pockets of the waist belt 120 of the fixation part 100 and sewn up to make the support part 200 fixed and supported in the fixation part 100.

The spring part includes a first coil spring 310 and a second coil spring 320. The first coil spring 310 forms a sleeve around the support part 200, the second coil spring 320 forms a sleeve around the first coil spring 310, and the bottom and the top of the first coil spring 310 and the second coil spring 320 are separately supported between the inverted Y-shaped part 210 and the Y-shaped part 220 of the support part 200. In this embodiment, the overhead projection of the first coil spring 310 is ellipse shaped, the overhead projection of the second coil spring 320 is ellipse shaped. In this embodiment, two adjacent spring rings of the first coil spring 310 are connected closely; two adjacent spring rings of the second coil spring 320 are connected closely. The second coil spring 320 are applicable to the longitudinal and central inner surface of the back of the user, making the ellipse spring close to the human skeleton when used. The body suit will keep its shape even when used for several years, and it is suitable for the body motion with protection function, comfortable and well look. In this embodiment, the first coil spring 310 and the second coil spring 320 are made of stainless steel.

The wearing part 400 includes a chest guard 410 and two straps 420. A second adjustable buckle 411 is disposed in the chest guard 410 to adjust the length of the chest guard 410. The chest guard 410 includes a front part and a back part, two second assembly belt of faced down are disposed inside the back part. Two ends of the strap 420 are separately connected to the front part and the back part of the chest guard 410. Two wearing belts of the wearing part 400 are separately connected to the two upper ends of the Y-shaped part 220 of the support part 200 and sewn up, making the wearing part 400 fixed and supported in the support part 200.

When used, the user puts on the pelvis fixation belt 100, and then adjusts the first adjustable buckle 121 to adjust the length of the waist belt 210 and fix it, making the waist belt 120 worn around the waist of the user and supported over the pelvis of the user. The chest guard 210 is worn around the chest, two hands pass through the two straps 420. The user adjusts the second adjustable buckle 411 to adjust the length of the chest guard 210 and fix it. Two straps and the chest guard are connected to the support part 200 to bear the gravity above the waist and the chest, the support part 200 is supported by the fixation part 100. It can relieve the extrusion pressure between the centrums of the lumbar and the thoracic vertebra.

In this embodiment, the cloth of the body suit is applied with infrared radiation, which can promote blood circulation with health care. The body suit has better to be disinfected that will not produce ill smell even without washed for 7 days. It is suitable to long term wear without ill smell.

Although the present invention has been described with reference to the preferred embodiments thereof for carrying out the patent for invention, it is apparent to those skilled in the art that a variety of modifications and changes may be made without departing from the scope of the patent for invention which is intended to be defined by the appended claims.

INDUSTRIAL APPLICABILITY

The present invention of a vertebra health body suit is provided. With the longitudinal support by the memory alloy support part and the spring part, the gravity above the chest and the waist is supported by the pelvis to relieve the force of the waist. The present invention is reasonable designed and easy to use with well industrial applicability.

What is claimed is:

1. A vertebra health body suit, comprising:
   a fixation part, which is removably surrounded to a waist of a user and supported on a pelvis of the user;
   a memory alloy support part, a lower end of which is fixed and supported on the fixation part;
   a spring part, which includes at least a first coil spring and a second coil spring, the first coil spring forming a sleeve around the support part and the second coil spring forming a sleeve around the first coil spring; and
   a wearing part, which is removably worn on a chest and a shoulder of the user, the wearing part assembled in an upper end of the support part.

2. The vertebra health body suit according to claim 1, further comprising:
   an inverted Y-shaped part fixed in the lower end of the support part,
   a Y-shaped part fixed in the upper end of the support part,
   two lower ends of the inverted Y-shaped part fixed to the fixation part,
   two upper ends of the Y-shaped part assembled to the wearing part.

3. The vertebra health body suit according to claim 1, wherein
   the first coil spring is ellipse shaped in plan view, and
   the second coil spring is ellipse shaped in plan view.

4. The vertebra health body suit according to claim 1, wherein
   two adjacent spring rings of the first coil spring are connected closely; and two adjacent spring rings of the second coil spring are connected closely.

5. The vertebra health body suit according to claim 1, wherein
the fixation part further includes a waist belt,
a length adjustable buckle is disposed in the waist belt; and
the lower end of the support part is fixed and supported in the waist belt.

6. The vertebra health body suit according to claim 1, wherein
the wearing part includes a chest guard and two straps,
the chest guard is provided with a length adjustable buckle, and
the chest guard is fixed and supported in the upper end of the support part.

\* \* \* \* \*